United States Patent [19]

Brader

[11] Patent Number: 4,993,592
[45] Date of Patent: Feb. 19, 1991

[54] METHOD FOR USE OF CONTAINER HAVING LID ACTIVATED AND METHODS THEREFOR

[76] Inventor: Allen C. Brader, 2160 Overhill Rd., Allentown, Pa. 18103

[21] Appl. No.: 443,928

[22] Filed: Nov. 30, 1989

Related U.S. Application Data

[62] Division of Ser. No. 383,162, Jul. 20, 1989, Pat. No. 4,905,825.

[51] Int. Cl.$^5$ .............................................. B67B 7/00
[52] U.S. Cl. ...................................... 222/1; 222/514; 222/523; 222/545; 206/221
[58] Field of Search ............... 206/219, 221; 222/1, 222/145, 513, 514, 515, 523, 545; 239/303

[56] References Cited

U.S. PATENT DOCUMENTS

| | | | |
|---|---|---|---|
| 2,756,129 | 7/1956 | Harris | 206/221 X |
| 3,651,207 | 3/1972 | Lauster et al. | 424/50 |
| 3,696,919 | 10/1972 | Miles | 206/221 |
| 3,772,431 | 11/1973 | Mlkvy | 424/44 |
| 3,856,138 | 12/1974 | Maekawa et al. | 206/221 |
| 3,888,976 | 6/1975 | Mlkvy et al. | 424/44 |
| 3,947,567 | 3/1976 | Berg, Jr. et al. | 430/618 |
| 4,024,952 | 5/1977 | Leitz | 206/221 |
| 4,132,770 | 1/1979 | Barth | 424/49 |

FOREIGN PATENT DOCUMENTS

8203212 9/1982 World Int. Prop. O. .

*Primary Examiner*—Andres Kashnikow
*Assistant Examiner*—Gregory L. Huson
*Attorney, Agent, or Firm*—Steele, Gould & Fried

[57] ABSTRACT

A method for storing, mixing, dispensing, and returning a fluid, a mixable composition and a resultant fluid meant for oral application includes the steps of providing a movable member within a cup-like container that isolates the mixable composition, containing the fluid about a portion of the movable member which isolates that composition, opening the container and displacing the movable member upwardly to concurrently mix the fluid and the mixable composition, accessing the resulting fluid for oral application by a user, and returning spent fluid to the container and closing the container. The method also may include the step of containing the discarded fluid separately.

7 Claims, 1 Drawing Sheet

METHOD FOR USE OF CONTAINER HAVING LID ACTIVATED AND METHODS THEREFOR

This is a division, of application Ser. No. 383,162 filed Jul. 20, 1989, now U.S. Pat. No. 4,905,825, dated Mar. 6, 1990.

BACKGROUND OF THE INVENTION

The present invention relates to a container for storing, mixing and dispensing a fluid mixed composition therefor.

In some situations, it is desirable to mix a small amount of solid material with a small amount of liquid, to form a fresh liquid mixture. One example is an effervescent mixture wherein an effervescing solid is mixed in water just prior to use, for example as an effervescent mouthwash, stomach remedy or the like. In those situations the user carries the solid composition in a separate container distinct from the container carrying the liquid until ready to use them. Also, the material must be mixed in the proper proportions before being used. Where the user adds liquid to any available container, there is a possibility of incorrect proportions. The present invention alleviates these problems by providing a compact structure carrying both the appropriate amounts of liquid and solids and enabling mixing immediately prior to use.

OBJECTS OF THE INVENTION

It is an object of the present invention to provide a container which stores, mixes and dispenses a fluid and a mixable composition without the necessity of having two distinct containers for these components.

It is another object of the present invention to provide a container which automatically mixes the mixable or solid composition and the fluid and provides a unique dispenser for the resulting fluid.

It is a further object of the present invention to provide a container which also incorporates a chamber for discarded fluid.

SUMMARY OF THE INVENTION

The container includes a housing with a liquid containment section, defined in part by a common wall, that holds the fluid. A movable member defines, in a first position and in conjunction with the common wall, a sealed interior chamber within which is disposed the mixable or solid composition. In a second position, the movable member is raised above the common wall thereby mixing the mixable composition and the fluid in a mixing section. The mixing section is a combination of the liquid containment section and the interior chamber. The container also includes a lid which is removably attachable to the housing and is operatively associated with the movable member such that when the lid is removed, the movable member is enabled to move from the first position to the second position. The container also includes a port for dispensing the resultant fluid derived from mixing the mixable composition and the fluid. The movable member has an open top and an open bottom. The bottom of the member sealingly engages the common wall and the open top is covered by the lid when the member is in the first position. In the second position, the open bottom, open top and the hollow body of the movable member define a passage between the mixing section and the exterior of the container thereby defining the port for dispensing the resultant fluid. The movable member can be biased to apply a force against the lid when in the first position and when the lid is removed, the member automatically moves to the second position. The method for storing, mixing and dispensing includes the steps of providing a movable member that isolates the mixable composition, containing the fluid about a portion of the movable member which isolates that composition, and substantially concurrently moving the member, exposing the mixable composition to the fluid and exposing the resultant fluid to the ambient environment.

BRIEF DESCRIPTION OF THE DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENT

Figure 1:
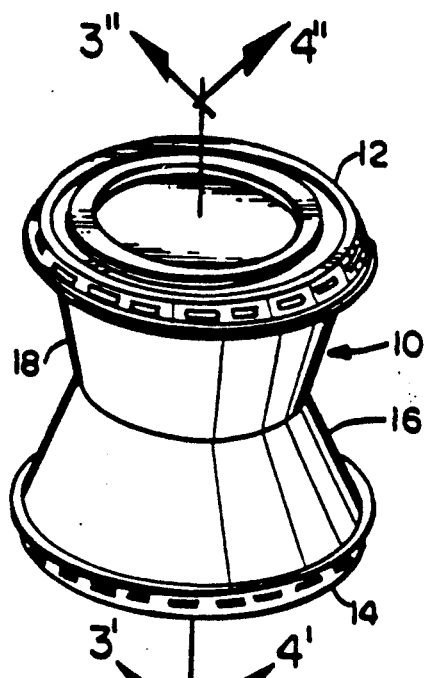
FIG. 1 illustrates a perspective view of the container.

The present invention relates to a cup-like container for storing, mixing and dispensing a fluid and one or more mixable compositions and a method therefor. FIG. 1 illustrates container 10 having a removable top lid 12 and a removable bottom lid 14. The external configuration of the container consists of a lower frusto-conical portion 16 having its radially smaller diameter attached to a similar diameter section of an upper frusto-conical portion 18.

Figure 2:
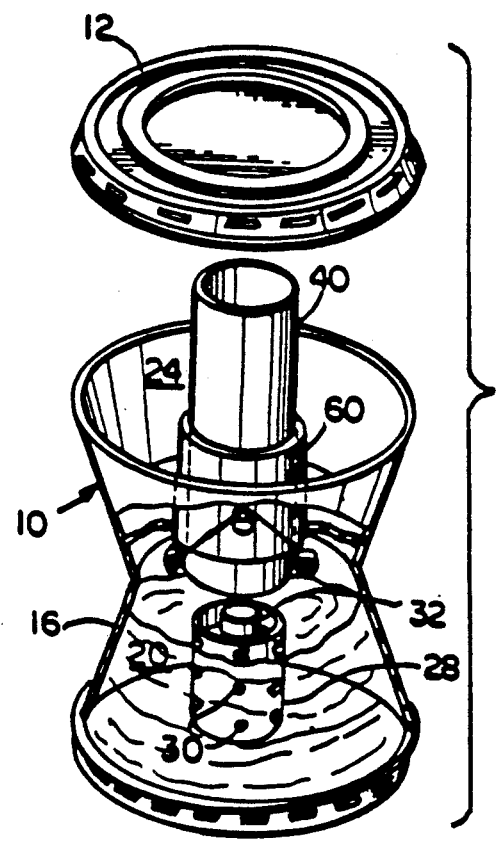
FIG. 2 illustrates an operational view of the container with the movable member in the second position wherein the preferably solid composition mixes with the fluid in the container.
Figure 3:
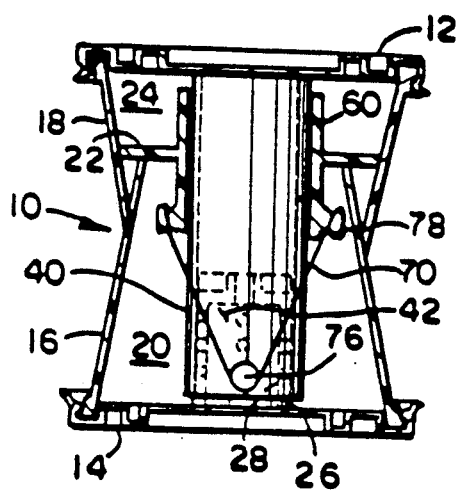
FIGS. 3 and 4, respectively, illustrate cross-sectional views of the container when the movable member is in the first position from the perspective of section lines 3'—3" and 4'—4" in FIG. 1.
Figure 4:
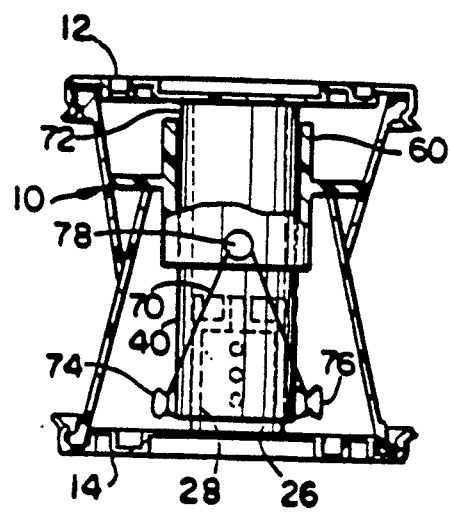

FIG. 2 is a view of container 10 with upper lid 12 removed from the container and the lower frusto-conical portion 16 section shown broken away and in cross-section to reveal the interior structure of the container. FIGS. 3 and 4, respectively, illustrate cross-sectional views of container 10 from the perspective of section lines 3'—3" and 4'—4" in FIG. 1. Reference will be made concurrently to FIGS. 2, 3 and 4.

With respect to FIG. 3, the interior of lower frusto-conical portion 16 defines a liquid containment section 20. Liquid containment section 20 extends upward into the lower regions of upper frusto-conical portion 18. Interior wall 22 separates and segregates liquid containment section 20 from a discard liquid containment section 24. Lower lid 14 is removably attached to lower frusto-conical portion 16 such that the fluid (shown in FIG. 2) can be placed within liquid containment section 20 when container 10 is inverted and lid 14 removed.

Lid 14 also defines a common wall 26. Attached to and extending above into the interior of container 10 is a composition holder 28. The mixable composition, which may be a solid, powder, another liquid, or gas, etc. and may react with the fluid is charged within composition holder 28. Composition holder 28 includes a plurality of laterally extending through passages, one of which is passage 30 shown in FIG. 2. The composition holder also includes at its top end, an upper passage 32 which permits the gas bubbles to rise vertically upward if the composition retained in holder 28 effervesces when placed in contact with the fluid stored within liquid containment section 20.

Disposed in the interior of container 10 is a movable member 40. Movable member 40 is operable between two positions, a first position shown in FIG. 3 and a second position referred to as an extended position shown in FIG. 2. In the first position (FIG. 3), movable member 40 has a lower extension which sealingly engages the exterior walls of composition holder 28. Alternatively, member 40 could directly engage common wall 26. Since the lower portion of composition holdre 28 can be considered part of lid 14, and hence part of common wall 26, movable member 40 sealingly engages both the common wall and the holder. When in the first position, the movable member defines a sealed interior chamber 42. The mixable composition is disposed within sealed interior chamber 42 when movable member 40 is in the first position. Movable member 40 is enabled to move from the first position (FIG. 3) to the second position (FIG. 2) when lid 12 is removed from container 10. For example in the illustrated embodiment, movable member 40 is a cylindrical tube that moves within a sleeve 60 extending both into discard fluid containment section 24 as well as into the principal liquid containment section 20. When lid 12 is removed, movable member 40 can be withdrawn or moved upwardly thereby exposing holder 28 and hence the mixable composition, which may be solid or powder rather than liquid, with the fluid contained in liquid containment area 20. The mixable composition would thereafter mix with the fluid and a resultant fluid or fluid and gas composition would be created. In the second position, movable member 40 also provides a port for the dispensing of the resultant fluid from a mixing section, consisting of the combination of the liquid containment section 20 and the interior chamber 42, to the exterior of the container or to the ambient environment.

In the illustrated embodiment, movable member 40 is biased by a rubberband or other spring or resilient mechanism 70 (FIG. 4) such that top region 72 of movable member 40 applies a force against lid 12. When lid 12 is removed, movable member 40 moves upward due to the spring force of biasing device 70. Thus top region 72 moves upward past the rim of cup-like container 10. If biasing device 70 is a rubberband, the rubberband is held or attached to the lower regions of member 40 via outwardly extending pins 74, 76. Rubberband 70 is further supported by pins extending outwardly from sleeve 60. One of the pins is pin 78 extending outward from sleeve 60.

To load or charge the container in the preferred embodiment, lid 14 is initially removed. The solid mixable composition is then placed within holder 28. When container is inverted such that the radially greater dimension of frusto-conical portion 16 faces upward, the fluid is placed within liquid containment section 20. Fluid is carefully placed within liquid containment section 20 such that no fluid enters the interior portions of member 40. Lid 14 is then placed on the container such that holder 28 and common wall 26 sealingly engages the lower regions of member 40. The container is then returned to its proper upright position as shown in FIGS. 3 and 4.

To use the container, upper lid 12 is removed and member 40 moves upward due to the biasing effect of spring or rubberband 70. At this time, the mixable solid composition in holder 28 mixes with the fluid in liquid containment section 20. Dependent upon the chemical reaction between these two or more elements, the resulting fluid may effervesce. Member 40 is a hollow body and includes an open top as well as an open bottom. Therefore, member 40 defines a port and a passage, or a conduit, to discharge the resulting fluid from the mixing section (the combination of liquid containment section 20 and interior chamber 42) to the ambient environment or to the exterior of the container. If the resulting fluid is a mouthwash, the discarded or used mouthwash can be returned to discharge fluid containment sections 20 and 24. Lid 12 can thereafter be attached to container 10 thereby sealing the spent fluid and any remaining fluid held in liquid containment section 20.

According to the above described operation, member 40 moves upward, exposing the mixable composition to the fluid, and exposing the resulting fluid to the ambient environment. This all occurs substantially concurrently.

It should be noted the mixable composition holder 28 may be an integral part of lower lid 14. In this case, it may be desirable to have the lower edge of member 40 extend completely down to contact and sealingly engage common wall 26 of lid 14.

The container, which is suitably adapted for use by persons in contained environments, e.g. patients in hospitals, nursing and assisted care facilities, passengers on airlines, the handicapped, may be charged with numerous oral hygenic mouthwashes, which are suited for achieving particular purposes, e.g. cleansing of the teeth, freshening of the breath, desensitizing teeth to hot and cold, and other oral hygienic applications. Typically, the mouthwash is one which contains at least one of a foaming material and an effervescing material, which on contact with a fluid generates an inert gas which promotes at least one of a foaming action and an effervescing action, and thereby increases the effectiveness of the contact of the resultant oral hygenic solution with the teeth and gums.

In a preferred embodiment of the container of this invention, holder 28 is filled with a preselected amount of a solid, e.g. an alkali metal carbonate or bicarbonate, often in combination with a solid acid, e.g. citric or tartaric acid. The alkali metal carbonate or bicarbonate, sodium or potassium carbonate or sodium or potassium bicarbonate serves multiple funtions, e.g. on contact with water, releases carbon dioxide and promotes foaming. The citric and tartaric acid enhances the rate at which carbon dioxide is formed and thus promotes foaming in the composition. In addition, tartaric or citric acid serves additional functions, e.g. tartaric and citric acids function as anti-oxidants and stabilizers.

Sleeve 60 then is placed over the holder 28 and movable member 40 moved to a first position, thereby sealing holder 28. Liquid containment section 20 then is charged with a preselected fluid which on mixing with the solid in holder 28 effects the desired oral treatment of the patient. Typically liquid containment section 20 is charged with an aqueous formulation containing astringents, flavorants, colors and sweeteners for mouthwash applications, as might be desired by passengers on airlines or persons in other restricted environments. Sweeteners and flavorants incude sacchrin, cinnamon, oil of clove, peppermint, and so forth. Other common additives in mouthwash and oral solutions include disodium salt of ethylenediaminetetraacetic acid (EDTA) which sequesters calcium in solution, preservatives such as sodium benzoate, benzoaic acid, desensitizing agents such as potassium nitrate or strontium nitrate, surfactants such as ethylene oxide, condensates of sorbitan monostearate; anionic surfactants such as sodium salts of monosulfated monoglycerides of hydrogenated coconut oil fatty acids, alkyl sulfates such as sodium laurylsulfate, alkylauryl sulfonates such as sodium dodecylbenzene sulfonate, and the like.

Illustrative oral hygienic solutions are described in U.S. Pat. Nos. 4,132,770; 3,772,431; 3,888,976; 3,651,207; and 3,947,567, all being incorporated by reference.

In operation a person utilizing the container will remove lid 12 which then permits movable member 40 within sleeve 60 to move to a second position position thereby exposing holder 28 to the fluid contained in liquid containment section 20. The alkyli metal carbonate or bicarbonate, for example, is contacted with the fluid in liquid containment section 20 by virtue of the passages 30 and carbon dioxide gases released. This release promotes mixing, and with mild agitation by a person using the container, carbon dioxide evolution may be enhanced. A person simply sips the oral hygienic solution from container 10, and then if desired may return the spent oral hygenic solution to container 10 and lid 12 placed over container 10 for disposal of the spent solution.

The claims appended hereto are meant to cover modifications and changes within the spirit and scope of the present invention.

What is claimed is:

1. A method for storing and mixing a fluid and a mixable composition, dispensing a resultant fluid which is a result of mixing said fluid and said mixable composition, and returning a spent fluid for storage, comprising the steps of:
   providing a movable member within cup-like container isolating said mixable composition;
   containing said fluid about a portion of said movable member which isolates said mixable composition;
   opening the container and displacing the movable member upwardly to concurrently mix the fluid and the mixable composition;
   accessing the resultant fluid by a user;
   returning the spent fluid to the container and closing the container.

2. A method as claimed in claim 1 further comprising: containing a spent fluid separate from said fluid; and attaching the lid,
   whereby the spent fluid may be sanitarily stored for disposal.

3. A method for storing and mixing a fluid and a mixable composition, dispensing a resultant fluid which is an oral hygienic solution and which is a result of mixing said fluid and said mixable composition, and returning a spent oral hygienic solution comprising the steps of:
   providing a movable member within a cup-like container isolating said mixable composition;
   containing said fluid about a portion of said movable member which isolates said mixable composition;
   opening the container and displacing the movable member upwardly to concurrently mix the fluid and the mixable composition;
   accessing the resultant fluid for oral application by a user;
   returning spent fluid to the container and closing the container.

4. A method as claimed in claim 3 further comprising:
   providing at least one of an effervescing material and a foaming material as the mixable composition; and
   providing a mouthwash as the fluid;
   whereby the resultant fluid will be the oral hygienic solution characterized by at least one of an effervescing action and a foaming action.

5. A method as claimed in claim 3 further comprising forming the movable member into a conduit disposed to extend upwardly beyond a rim of the cup-like container, and wherein said accessing comprises pouring the resultant fluid through a port and a passage formed by the movable member in an extended position.

6. A method as claimed in claim 5 further comprising providing the movable member with a resilient means biasing the movable member to the extended position.

7. A method as claimed in claim 6 further comprising confining the movable member under a lid, wherein closing the container includes pushing the movable member back down into the container with the lid.

* * * * *

UNITED STATES PATENT AND TRADEMARK OFFICE
CERTIFICATE OF CORRECTION

PATENT NO. : 4,993,592
DATED : February 19, 1991
INVENTOR(S) : Allen C. Brader

It is certified that error appears in the above-identified patent and that said Letters Patent is hereby corrected as shown below:

IN THE TITLE: delete the words "AND METHODS THEREFOR" and insert therefor -- MIXING MECHANISM --

Signed and Sealed this

Fourth Day of August, 1992

Attest:

DOUGLAS B. COMER

Attesting Officer

Acting Commissioner of Patents and Trademarks